US009867567B2

(12) United States Patent
Cordes

(10) Patent No.: US 9,867,567 B2
(45) Date of Patent: Jan. 16, 2018

(54) BLINDING KIT FOR CLINICAL TRIALS

(71) Applicant: SANOFI-AVENTIS DEUTSCHLAND GMBH, Franfurt am Main (DE)

(72) Inventor: Claus Cordes, Frankfurt am Main (DE)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 310 days.

(21) Appl. No.: 14/371,778

(22) PCT Filed: Jan. 15, 2013

(86) PCT No.: PCT/EP2013/050640
§ 371 (c)(1),
(2) Date: Jul. 11, 2014

(87) PCT Pub. No.: WO2013/107723
PCT Pub. Date: Jul. 25, 2013

(65) Prior Publication Data
US 2014/0350468 A1  Nov. 27, 2014

(30) Foreign Application Priority Data

Jan. 16, 2012  (EP) ................................. 12151198

(51) Int. Cl.
*A61B 5/00* (2006.01)
*A61M 5/19* (2006.01)
(Continued)

(52) U.S. Cl.
CPC ........... *A61B 5/4848* (2013.01); *A61M 5/002* (2013.01); *A61M 5/19* (2013.01); *A61M 5/20* (2013.01);
(Continued)

(58) Field of Classification Search
CPC .. A61B 5/4848; A61B 5/002; A61M 5/31566; A61M 5/16827;
(Continued)

(56) References Cited

U.S. PATENT DOCUMENTS 3,834,387 A * 9/1974 Brown .............. A61M 5/31513
141/27
4,795,441 A * 1/1989 Bhatt ................... A61G 7/0503
128/DIG. 26
(Continued)

FOREIGN PATENT DOCUMENTS

DE        19912434      9/2000
EP        0721805       7/1996
(Continued)

OTHER PUBLICATIONS

International Search Report for Int. App. No. PCT/EP2013/050640, dated May 27, 2013.
(Continued)

*Primary Examiner* — Aarti B Berdichevsky
*Assistant Examiner* — Hamza Darb
(74) *Attorney, Agent, or Firm* — McDonnell Boehnen Hulbert & Berghoff LLP

(57) ABSTRACT

A blinding device for administering a substance to a patient in a clinical trial is presented where the blinding device has an opaque housing to receive at least two delivery devices adapted to dispense a substance provided therein, an outlet being in fluid communication with at least one delivery device for administering the substance to a patient, and at least one actuating member mechanically engageable with at least one delivery device and being actuatable from outside the housing.

13 Claims, 7 Drawing Sheets

(51) Int. Cl.
*A61M 5/315* (2006.01)
*A61M 5/00* (2006.01)
*A61M 5/20* (2006.01)
*A61M 5/31* (2006.01)
*A61M 5/168* (2006.01)

(52) U.S. Cl.
CPC .... *A61M 5/31511* (2013.01); *A61M 5/31566* (2013.01); *A61M 5/16827* (2013.01); *A61M 2005/3125* (2013.01); *A61M 2202/0468* (2013.01)

(58) Field of Classification Search
CPC .. A61M 2005/3125; A61M 2202/0468; A61M 5/002; A61M 5/20; A61M 5/19; A16M 5/31511
See application file for complete search history.

(56) References Cited

U.S. PATENT DOCUMENTS

| | | | | |
|---|---|---|---|---|
| 5,411,490 | A | * | 5/1995 | Tennican et al. |
| 5,454,792 | A | * | 10/1995 | Tennican ............ A61M 5/1408 137/625.11 |
| 5,658,248 | A | | 8/1997 | Klein et al. |
| 6,350,987 | B1 | * | 2/2002 | Northrup ................ H01J 49/04 250/282 |
| 6,544,250 | B1 | * | 4/2003 | Schaffer ................ A61D 7/00 206/438 |
| 2008/0167621 | A1 | | 7/2008 | Wagner et al. |
| 2008/0255520 | A1 | * | 10/2008 | Henderson ............ A61M 5/19 604/191 |

FOREIGN PATENT DOCUMENTS

| | | |
|---|---|---|
| JP | S44-018518 | 8/1969 |
| JP | S60-154684 | 10/1985 |
| JP | 2002-529151 | 9/2002 |
| JP | 2008-540117 A | 11/2008 |
| WO | 2004/004802 | 1/2004 |
| WO | 2006/060688 | 6/2006 |
| WO | 2011/154928 | 12/2011 |

OTHER PUBLICATIONS

International Preliminary Report on Patentability for Int. App. No. PCT/EP2013/050640, dated Feb. 27, 2014.

* cited by examiner

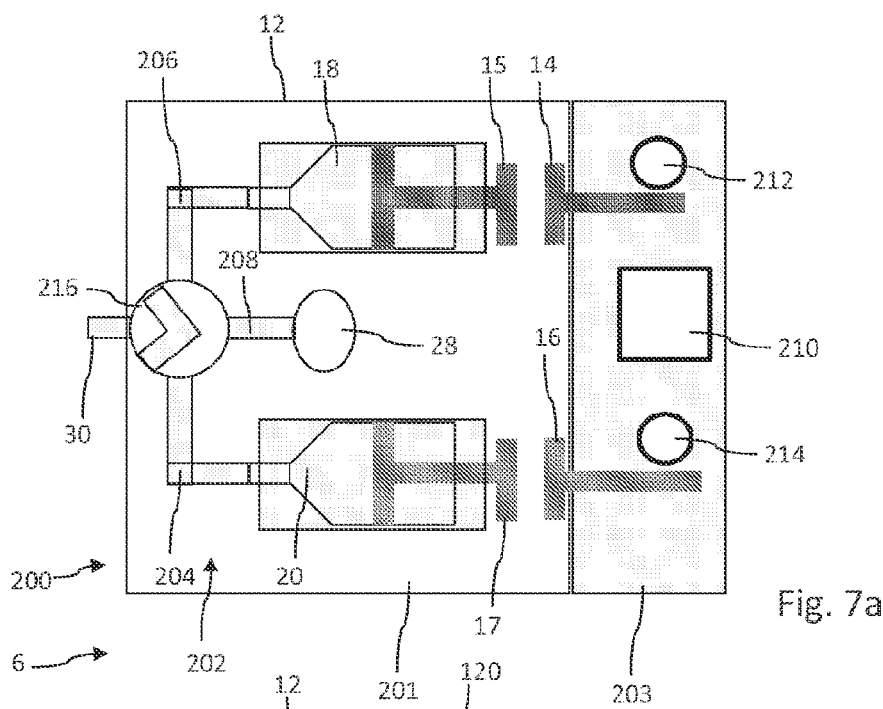
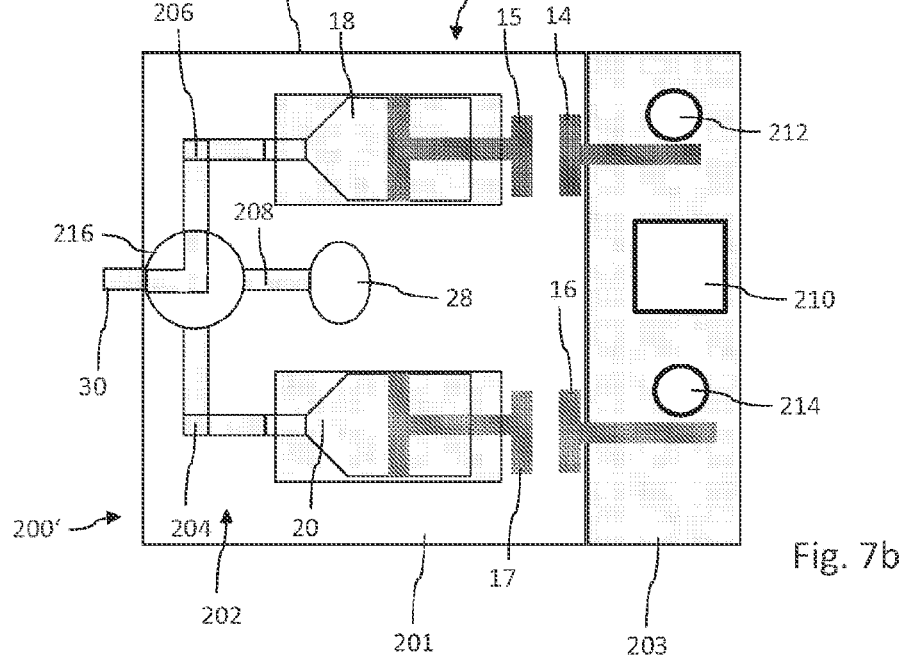

BLINDING KIT FOR CLINICAL TRIALS

CROSS REFERENCE TO RELATED APPLICATIONS

The present application is a U.S. National Phase Application pursuant to 35 U.S.C. §371 of International Application No. PCT/EP2013/050640 filed Jan. 15, 2013, which claims priority to European Patent Application No. 12151198.4 filed Jan. 16, 2012. The entire disclosure contents of these applications are herewith incorporated by reference into the present application.

TECHNICAL FIELD

The present invention relates to the field of clinical trials and in particular to a blinding kit for administering a medicament to a patient in clinical trials. The blinding kit is particularly adapted to conceal whether a medicament or an inert substance is provided and administered to the patient.

BACKGROUND

In clinical studies or trials, effectiveness of a medicament can be proved by treating a group of patients with a medicament while treating a comparative group of patients with an inert or inactive substance, like a physiological saline solution, substantially acting as a placebo.

However, depending on the type of administration of the medicament and depending on generic properties of the medicament, it may be inadmissible to administer the inert substance to the patient. If for instance a parenteral medicament features a particular colour it would be inadmissible to dye a comparative inert substance accordingly. In such cases, administration of the inert substance to the patient has to be pretended or simulated. However, neither patient nor medical staff should become aware of the pretended administration of the medicament.

Document U.S. Pat. No. 6,544,250 B1 for instance describes a device for blinding the administration of non-solid pharmaceutical presentations in clinical trials without using the so-called double-blind technique. This device is particularly designed for intrapulmonary administration of a medicament. The device comprises a blinding bag having at least two attachments. One of said attachments is intended for connection to a dispenser for the pharmaceutical presentation and the other attachment is intended for connection to an applicator.

The inside of said bag has means for holding back the pharmaceutical presentation, wherein the attachment intended for connection to the applicator has a closure inside the container. Another embodiment of said blinding bag comprises two similar attachments, wherein the attachments have a continuous connection in the inside of the container, thus ensuring that the pharmaceutical presentation is transported through the container.

However, such blinding device is not suitable for clinical trials, in which the medicament has to be administered to the patient by way of injection. Also when holding back the pharmaceutical presentation, the blinding bag may gain weight which may be perceptible by either medical staff or by the patient, thereby increasing a risk of unblinding.

It is therefore an object of the present invention to provide a blinding device and a blinding kit being universally applicable to different kinds of administration of medicaments, pharmaceutical substances as well as to inert or placebo substances. It is a further aim to increase patient safety and to improve the blinding of pharmaceutical or inert substances and to reduce a risk of unblinding, both to the patient as well as to medical staff.

SUMMARY

In a first aspect a blinding device for administering a substance to a patient in a clinical trial is provided. The blinding device comprises an opaque housing to receive at least two delivery devices, each of which being adapted to dispense a substance provided therein. The blinding device, in particular its housing further comprises an outlet adapted to become engaged with at least one of the two delivery devices in a fluid communicating or fluid-transferring way for administering the substance to a patient.

Furthermore, the blinding device comprises at least one actuating member mechanically engageable with at least one delivery device and being actuable from outside the housing. This way, a substance-containing delivery device, such like a medicament or placebo-containing cartridge or syringe is to be entirely displaced inside an opaque housing. Operation of the delivery device is to be conducted or executed from outside the housing by at least one actuating member. This way it is effectively concealed which of the at least two delivery devices is subject to a dispensing action induced by the actuating member.

In a first aspect, this offers to conceal a fluid path downstream of the two delivery devices and upstream of the outlet. In a second aspect, the blinding device may additionally or alternatively offer to conceal mechanical engagement or mechanical coupling between the actuating member extending outside the housing and the delivery device displaced entirely inside the housing.

Independent whether mechanical interaction between actuating member and delivery device or whether a fluid path downstream the delivery device is concealed, the blinding device is beneficial in terms of not gaining weight when used to conceal administration of an inert substance or of a placebo. Since the delivery devices filled with the substance to be dispensed or to be administered to the patient via the outlet of the blinding device are pre-arranged inside the opaque housing, even an eventual collecting or retaining of a substance inside the housing of the blinding device does not lead to an increase of the blinding device's weight. This way, a risk of unblinding due to an increase of weight of the blinding device can be advantageously reduced.

In a preferred aspect the blinding device comprises at least two actuating members extending outside the housing. Here, each one of the actuating members is mechanically engageable with only one of the at least two delivery devices for separately and sequentially dispensing a substance from the respective delivery device. Preferably, each one of the at least two actuating members is directly mechanically engageable with one of the at least two delivery devices.

Hence, a proximal end section of each actuating member may extend outside the housing, e.g. through a sidewall thereof. An opposite, distal end of the respective actuating member may then be directly engageable with one of the at least two delivery devices. This way, a driving motion or thrust exerted by a user may be directly and/or substantially unalteredly transferred to the delivery device. Moreover, the delivery devices and their associated actuating members are substantially decoupled from each other. They are therefore actuatable in a separate and sequential way.

In a preferred aspect, the housing of the blinding device comprises a first compartment and a second compartment separated from each other, preferably by a dividing wall.

The first compartment is particularly adapted to receive the at least to delivery devices. However, the blinding device is not limited to only two delivery devices. It is generally conceivable, that the blinding device receives three or even more delivery devices, such like carpules, cartridges and/or syringes. Here, it is of particular benefit, when all delivery devices to be operated by the at least one actuating member are arranged in the first compartment.

Further and according to another preferred embodiment, the first compartment is accessible through a lockable lid for inserting and/or exchanging at least one delivery device. This way, a blinding device can be used with a large variety of different delivery devices and can be therefore universally adapted for usage of different pharmaceutical forms and medicaments.

In a further preferred embodiment, the first compartment further comprises at least two receptacles at least one of which being mechanically encoded to exclusively receive a particular type of delivery device. By mechanically encoding at least one of two receptacles provided in the first compartment, only such delivery devices featuring a corresponding geometric shape can be positioned in such a receptacle. This way, a risk of unintentional swapping of delivery devices filled with different substances can be minimized.

Moreover, by providing mechanically encoded receptacles, a fluid interconnection between the outlet of the blinding device and outlet ports of the respective delivery devices can be standardized. This way, different delivery devices can in principle be provided with identical connecting ports or connectors. Hence, all delivery devices could be provided with e.g. female connectors of e.g. Luer lock type, thereby impeding that the delivery devices can be used for direct administering, e.g. in connection with a piercing element or cannula featuring a female Luer lock as well.

According to a further embodiment, the second compartment is inaccessible from outside and is further adapted to conceal a correlation between the at least one actuating member and a flow path upstream of the outlet or downstream of the delivery devices. The inside configuration of the second compartment is therefore non-visible, neither to a patient nor to medical staff. The second compartment therefore provides a blinding functionality of the blinding device and effectively conceals a correlation or interrelation between actuation of the at least one actuating member and the type of substance to be dispensed from the outlet in response thereof.

According to a further embodiment, the second compartment is arranged adjacent the first compartment and is positioned downstream of the at least two delivery devices. In this embodiment, the second compartment provides a fluid communication between at least one of the delivery devices and the outlet. Depending on whether the blinding device is designed as a placebo device or as a verum device, intended to administer a pharmaceutically inert or inactive substance or to administer a medicament, respectively, the second compartment either provides a fluid communication between the outlet and a placebo-type delivery device or between the outlet and a verum-type delivery device.

Which one of the at least two delivery devices is actually in fluid communication with the outlet can be effectively concealed by the second compartment.

When the second compartment is arranged downstream of the at least two delivery devices, each outlet of the delivery devices is connected with a tubing system extending through a dividing wall that separates first and second compartments. Individual tubings extending into the first compartment and being in fluid communication with the delivery devices, respectively, either merge into the outlet extending outside the housing, in particular when the blinding device is of verum-type. Alternatively, when the blinding device serves as a placebo device, at least one tubing downstream of a delivery device is disconnected from the outlet.

Therefore and according to a further preferred embodiment, the second compartment may comprise a collecting reservoir to be coupled with at least one of the delivery devices, in particular with the medicament-containing delivery device, in a fluid transferring way to receive and/or to collect the entirety of the substance dispensable by said particular delivery device. Preferably, the collecting reservoir is provided with a hydrophilic and/or liquid absorbing substance. Hence, when the medicament-containing delivery device is operated, the medicament contained therein is simply dispensed into the reservoir but does not leave the opaque housing of the blinding device.

Since the medicament dispensed by the particular delivery device was already disposed inside the opaque housing prior to execution of the dispensing action, the overall weight of the housing of the blinding device remains substantially constant during such a mock actuation of the actuating member. Since the opaque housing has to accommodate at least two delivery devices in their entirety, overall dimensions of the opaque housing have to be adapted accordingly. A rather large housing may also come along with an increase of overall weight of the blinding device, thereby inherently minimizing a risk of unblinding due to weight modifications of the blinding device during operation.

Moreover, it is further conceivable, to arrange one or several supplemental ballast elements inside the opaque housing to conceal that the placebo-type blinding device features a reduced degree of weight loss compared to a verum-type blinding device.

According to another preferred embodiment, the second compartment comprises at least one mechanical transfer element being mechanically engaged with the at least one actuating member and being further mechanically engageable with at least one of the delivery devices arranged in the first compartment. In this embodiment, the second compartment is typically arranged adjacent an actuating side or portion of the at least two delivery devices. Here, a tubing downstream of the delivery devices may be accessible and visible, for instance when the first compartment is opened.

Moreover, the second compartment conceals mechanical engagement and mechanical interaction between the at least two delivery devices and the at least one actuating member extending through a lateral side wall of the opaque housing. In a simple embodiment featuring two delivery devices positioned in the first compartment, the second compartment provides two thrust transferring elements cooperating with the two delivery devices, wherein one of said thrust transferring elements is of dummy or mock-type.

With a placebo-type blinding device, actuation of the actuating member leads to a dispensing of the delivery device that contains an inert or pharmaceutically inactive substance while with a verum-type of blinding device, actuation of the actuating member leads to a dispensing of the other delivery device filled with the medicament. From outside, the different types of blinding devices are not distinguishable. The first compartments of the verum-type delivery device and the placebo-type delivery device are substantially identical. It is only the second compartment of a placebo-type blinding device that differs from a respective second compartment of a verum-type blinding device.

According to another embodiment, the thrust transferring element is slideably disposed in the second compartment and extends into the adjacently arranged first compartment with a pressure piece. The pressure piece of the transfer element is particularly adapted to transfer thrust or mechanical pressure to the delivery device positioned and fixed in the adjacently located first compartment.

When the second compartment is adapted to conceal mechanical interaction and engagement between the at least one actuating member and the at least two delivery devices it is of particular benefit, that operation or actuation of the actuating members is only possible when the lid of the first compartment is closed. Moreover, when the lid of the first compartment is opened and when pressure pieces of the transfer elements are thus at least visually inspectable, operation of the at least one, preferably of all actuating members is effectively impeded and prevented for not revealing or unblinding the mechanical interaction or correlation between the actuating member and the pressure pieces.

It is further of particular benefit, when the first compartment comprises a mock or dummy delivery device operably engageable with at least one actuating member. The mock delivery device is further adapted to imitate or to simulate mechanical resistance usually provided by a genuine delivery device when operated. This way, a placebo-type dummy device has no longer to be equipped or provided with a delivery device filled with a medicament or placebo. Since the mock delivery device is adapted to provide a mechanical feedback to a user being substantially identical or corresponding to a mechanical feedback provided by a genuine or real delivery device when operated, a user will not be able to distinguish from the mechanical feedback, whether he is operating or handling a verum-type blinding device or a placebo-type blinding device.

This way, the placebo-type blinding device in general does no longer require to be provided with a pharmaceutically active substance. Moreover, such an embodiment is of particular benefit in constellations, wherein it would be inadmissible to administer the placebo to the patient. This way, neither an inert nor a pharmaceutically active substance, like a medicament, have to be administered to the patient.

In a further preferred embodiment, a release of the lid covering the first compartment is effectively impeded by an interlock operably engaged with the at least one actuating member. Preferably, mutual or operable engagement between lid, interlock and/or actuating member is designed such, that the interlock releases the lid only when the actuating member or when all actuating members are in an initial configuration, in which a mechanical interrelation between actuating member and pressure pieces extending into the first compartment is not detectable. Moreover, the lid also impedes a displacement of the actuating member when in an opened configuration. This way, actuation or displacement of the actuating member is only released when the lid effectively closes the housing and its compartments.

Furthermore and according to another preferred embodiment, the blinding device comprises at least one delivery device disposed inside the housing which is at least partially filled with a medicament. It is conceivable, that the entire blinding device is pre-assembled with the at least two delivery devices in such a way, that the blinding device is ready to use. The entire blinding device may be further designed as a disposable device, wherein the lid covering the first compartment is of non-releasable type. After use of the blinding device, the entire device is to be discarded.

Alternatively, it is also conceivable, that the blinding kit is of reusable type in such a way, that the at least one actuating member can be returned into an initial position or configuration, in which the lid of the first compartment can be opened for replacement of at least one of the delivery devices.

According to another embodiment the blinding device further comprises at least one electrical drive to operably engage with the at least one delivery device and/or to engage with the at least one actuating member. By means of the electrical drive the actuating member is still actuatable from outside the housing. Here, activation of the electrical drive requires actuation of a respective control element, such like a switch or bottom accessible from outside the housing. Preferably, such control element might be integrated into the housing. It may be designed as an integrated input/output unit, by way of which a user may configure and control actuation of the at least one electrical drive.

It is of particular benefit when the electrical drive is exclusively operable when the blinding device is closed so that an electrically driven actuation of the at least one delivery device is not observable or trackable from outside the device. Also here, it is of particular benefit when the electrical drive is provided in the second compartment while the two delivery devices are arrangeable in the respective first compartment. When implementing an electrical drive in the blinding device it is of particular benefit, that neither the delivery device nor the at least one actuating member extend outside the housing of the blinding device. In this way, any fluid dispensing actuation of the electrical drive remains invisible and non-detectable from outside the blinding device.

It is particularly intended that each delivery device is separately coupled or engageable with a single electrical drive. Preferably, the at least one electrical drive is coupled and controlled by a control unit, which may decide according to a predefined schedule, whether the electrical drive operably engaged with the verum-type delivery device, or whether the electrical drive operably engaged with the placebo-type delivery device is to be actuated.

In this context it is conceivable that a particular patient identification number is entered into a control unit via an input/output module. If the particular patient belongs to a placebo group of patients, the respective electrical drive operably engaged with the placebo-type delivery device will be activated in a delivery or dispensing procedure.

With an electrical drive implemented in the blinding device it is of particular benefit that the blinding device is designed as a re-usable device. In this case, at least the delivery device mechanically engageable with the electrical drive should be releasably arrangeable in the respective compartment of the blinding device. In this way, the blinding device can be used repeatedly by simply exchanging a used delivery device.

For hygienic reasons it is of particular benefit and according to another embodiment when the at least first and second delivery devices are mutually coupled by means of a tube system. Preferably, the tube system is a hermetically sealed and closed system. In preferred embodiments the tube system may even comprise or form the outlet of the blinding device. Preferably, the first and second delivery devices together with the tube system interconnecting said delivery devices and/or the outlet port are removably insertable into a respective compartment of the blinding device while the at least one electrical drive is arranged in an other, i.e. adjacently disposed compartment.

By means of a closed and sterilized tube system only the first and second delivery devices and the interconnecting tube system have to be designed as disposable components that are to be discarded after use. The electrical drive and/or the at least one actuating member that serve to transfer a dispensing motion to the delivery devices may be reset in an original configuration before the blinding device is opened for removal of first and/or second delivery devices and the interconnecting tube system. In this way, the blinding device comprising comparatively expensive electrical drives can be used several times.

In still another embodiment, the tube system further comprises at least one remotely actuatable control valve. This embodiment is of particular use where the outlet is integrated into the tube system. Here, it is conceivable that the electrical drive or an accessory drive is operable to actuate and to manipulate the control valve. Preferably, the control valve is completely arranged inside the opaque housing of the blinding device. Its configuration cannot be determined from outside the device.

In this way, even a dispensing program or dispensing schedule could be implemented, wherein in a first step a pharmaceutically inactive substance is dispensed. In a second and subsequent step the pharmaceutically active substance could be dispensed by manipulating the control valve and by activating the electrical drive operably engaged with a respective delivery device. After the dispensing procedure has terminated the system may switch back into the first configuration to flush the tube system, e.g. with the pharmaceutically inert substance, e.g. with physiological saline solution.

Additionally or alternatively, the control valve may be connected to a collecting reservoir which may also belong to the closed tube system. In this way, and irrespective on whether the blinding device is implemented as a verum-type device or as a placebo-type device the final configuration of the interchangeable tube systems may always resemble. With the placebo-type device the pharmaceutically active substance will be collected in the collecting reservoir while with the verum-type blinding device it will be the pharmaceutically inert substance that accumulates in the collecting reservoir. Upon exchanging or removing the closed tube system the end user won't be able to identify whether a pharmaceutically active or inactive substance has been dispensed and provided to the patient.

With the tube system and with the at least one electrical drive a configuration or reconfiguration of the blinding device can be implemented by means of a software of the control unit. The placebo-type blinding device and the verum-type blinding device may therefore comprise substantially identical structural features and properties.

According to a further aspect, the invention also relates to a blinding kit for administering a substance to a patient in a clinical trial. The blinding kit comprises a first blinding device as described above and a second blinding device as describe above. Furthermore, first and second blinding devices are identically equipped and configured with delivery devices of different type, e.g. of delivery devices filled with an inert substance or a placebo and with delivery devices containing a pharmaceutically active substance, such like a medicament.

The first blinding device is particularly adapted to impede dispensing of a substance to the outlet. Said substance is contained in a particular delivery device, which in response of an actuation of an actuating member may provide a respective force feedback to a user. However, the mechanical coupling between the actuating member and the delivery device is such that the delivery device is actually not actuated or that actuation of the device does not lead to a dispensing of the substance at the outlet of the housing, which is preferably of rigid type.

In effect, the first blinding device is typically designed as a placebo-type blinding device.

The second blinding device is typically configured to allow dispensing of the substance contained in a comparable delivery device to the outlet in response of an actuation of the respective actuating member being operably coupled with said particular delivery device. First and second blinding devices are of identical shape and geometry such that neither patient nor medical staff becomes enabled to distinguish, which of first and second blinding devices is designed as a placebo-type device and which of the devices is designed as a verum-type blinding device.

In a further preferred embodiment, the first blinding device comprises a collecting reservoir to receive and/or to collect the substance dispensable from a first delivery device coupled therewith. Accordingly, the second blinding device provides a fluid communication between a respective first delivery device and the outlet of the blinding device.

In still another embodiment, first and second blinding devices comprise actuating members of substantially identical appearance and/or geometric shape which at least partially extend outside the housing of respective blinding devices. Here, the first delivery device of the first blinding device is operably disengaged from a first actuating member while the first delivery device of the second blinding device is operably engaged with the first actuating member.

The term "drug" or "substance", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H—His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the pertinent art that various modifications and variations can be made to the present invention without departing from the spirit and scope of the invention. Further, it is to be noted, that any reference signs used in the appended claims are not to be construed as limiting the scope of the present invention.

BRIEF DESCRIPTION OF THE DRAWINGS

In the following, preferred embodiments of the invention will be described in greater detail by making reference to the Figures, in which:

FIG. 7a shows another embodiment of a blinding device comprising an electrical drive in a first configuration, and FIG. 7b is indicative of the embodiment according to FIG. 7a in a second configuration.

DETAILED DESCRIPTION

Figure 1:
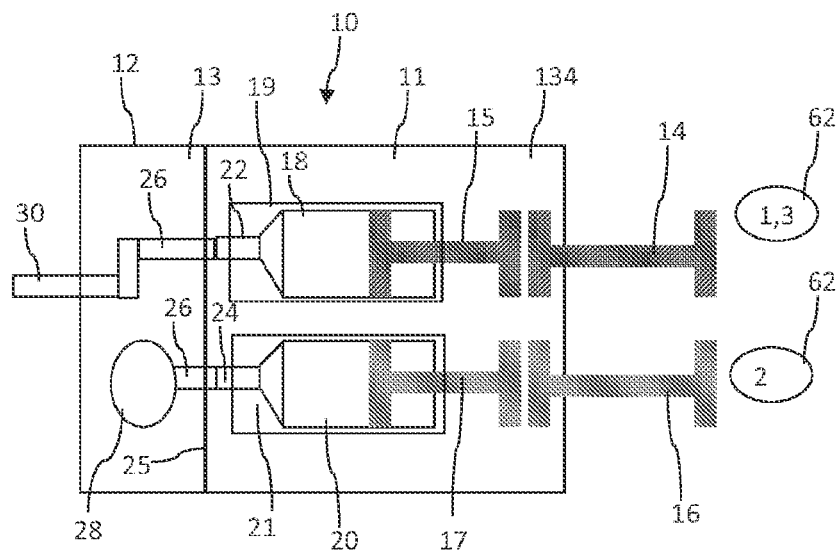
FIG. 1 shows a first embodiment of a blinding kit, wherein each blinding device comprises two delivery devices.
Figure 1:
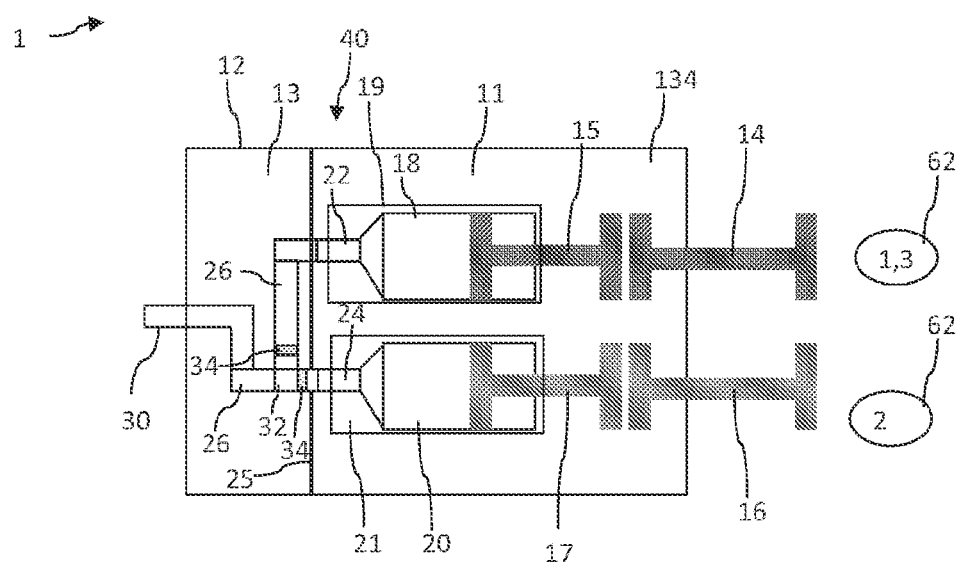

The blinding kit 1 as illustrated in FIG. 1 comprises a first blinding device 10 and a second blinding device 40. Each of the blinding devices 10, 40 comprises an opaque housing 12 having a first compartment 11 and a second compartment 13. The housings 12 are preferably of rather rigid type so as to conceal their inner structure. The two compartments 11, 13 are divided by a dividing wall 25. The blinding devices 10, 40 further comprise an outlet 30, by way of which a liquid substance contained in the blinding device 10, 40 can be administered to a patient in many different ways.

Even though the set of embodiments as illustrated in FIGS. 1 to 5 is based on syringe-type delivery devices, the invention is by no way limited to administering by way of dispensing or injection. Generally, the blinding kits 1, 2, 3, 4, 5 as illustrated in FIGS. 1 to 5 can be adapted and modified to various parental forms of administering liquid substances to a patient, e.g. also intrapulmonary.

The blinding devices 10, 40 are substantially identical apart from the functionality of the second compartment 13. As illustrated in FIG. 1, the second compartment 13, which is inaccessible to a user comprises a collecting reservoir 28 in fluid connection with a delivery device 20 being typically filled with a pharmaceutically active substance, e.g. with a medicament. The second compartment 12 further comprises a tubing 26 upstream of the outlet 30 which is in downstream fluid communication with the delivery device 18 being typically filled with an inert or physiological solution, such like with a saline solution.

As further indicated in FIG. 1, the first compartment 11 which is adapted to receive the delivery devices 18, 20 in receptacles 19, 21 or sub compartments. Upon insertion of the delivery devices 18, 20 into the compartment 11, respective outlets 22, 24 of the delivery device 18, 20 are to be interconnected with either the tubing 26 or with the collecting reservoir 28, respectively. Since the internal structure and function of the second reservoir 13 is concealed to the user, the user will be unable to identify, whether the blinding device 10 is of placebo- or of verum-type.

As further indicated in FIG. 1, the first compartment 11 further comprises receptacles 19, 21, each of which being particularly adapted to exclusively receive and to exclusively accommodate only a particular type of delivery device 18, 20. Preferably, the delivery device 18 filled with an inert substance is mechanically encoded to mate with the encoding of the receptacle 19. Accordingly, delivery device 20 can only be arranged in the receptacle 21. Regarding their fluid interconnection between outlets 22, 24 and corresponding connecting ports extending through the dividing wall 25, the two blinding devices 10, 40 are substantially identical.

In the illustrated embodiments, the delivery devices 18, 20 comprise a tubular shaped barrel, in which a piston 15, 17 is slideably displaced. A proximal end of the pistons 15, 17, facing away from the outlet 22, 24 is further to be mechanically engaged with a respective actuating member 14, 16, each of which extending outside the housing 12 of the respective blinding devices 10, 40. The actuating members 14, 16 illustrated as being of piston-type can be separately actuated in order to sequentially dispense a substance from the delivery device 18 and to dispense a substance from the delivery device 20.

Since the tubing 26 downstream of the delivery devices 18, 20 may feature a non-negligible volume, it may be beneficial to initially flush the tubing 26 by means of the substance provided by the delivery device 18 prior to dispense the medicament provided in the delivery device 20 by actuating the respective actuating member 16.

Moreover, after dispensing a particular amount of the medicament from the delivery device 20, a residual portion of the medicament may remain in the tubing 26 downstream of a y-connector 32 of the blinding device 40. In order to administer this residual amount, the other actuating member 14 can be repeatedly operated and depressed, e.g. in order to flush the tubing 26 with the inert substance.

As further illustrated in the sketch of FIG. 1, the tubing portions 26 upstream of the y-connector 32 are both provided with check-valves 34 in order to prevent back-flow of e.g. the medicament from delivery device 20 towards delivery device 18 and vice versa.

The blinding devices 10, 40 may further comprise a label 62 in order to indicate to a user, in which sequence the various actuating members 14, 16 have to be operated and/or depressed. Overall handling of both blinding devices 10, 40 is substantially identical. Due to the missing fluid communication between delivery device 20 and outlet 30 of the placebo-type blinding device 10, usage of this particular blinding device 10 does not provide administering a medicament to a patient. Instead, the medicament contained in the device 20 is simply dispensed into the collecting reservoir 28 but does not leave the device 10.

Figure 2:
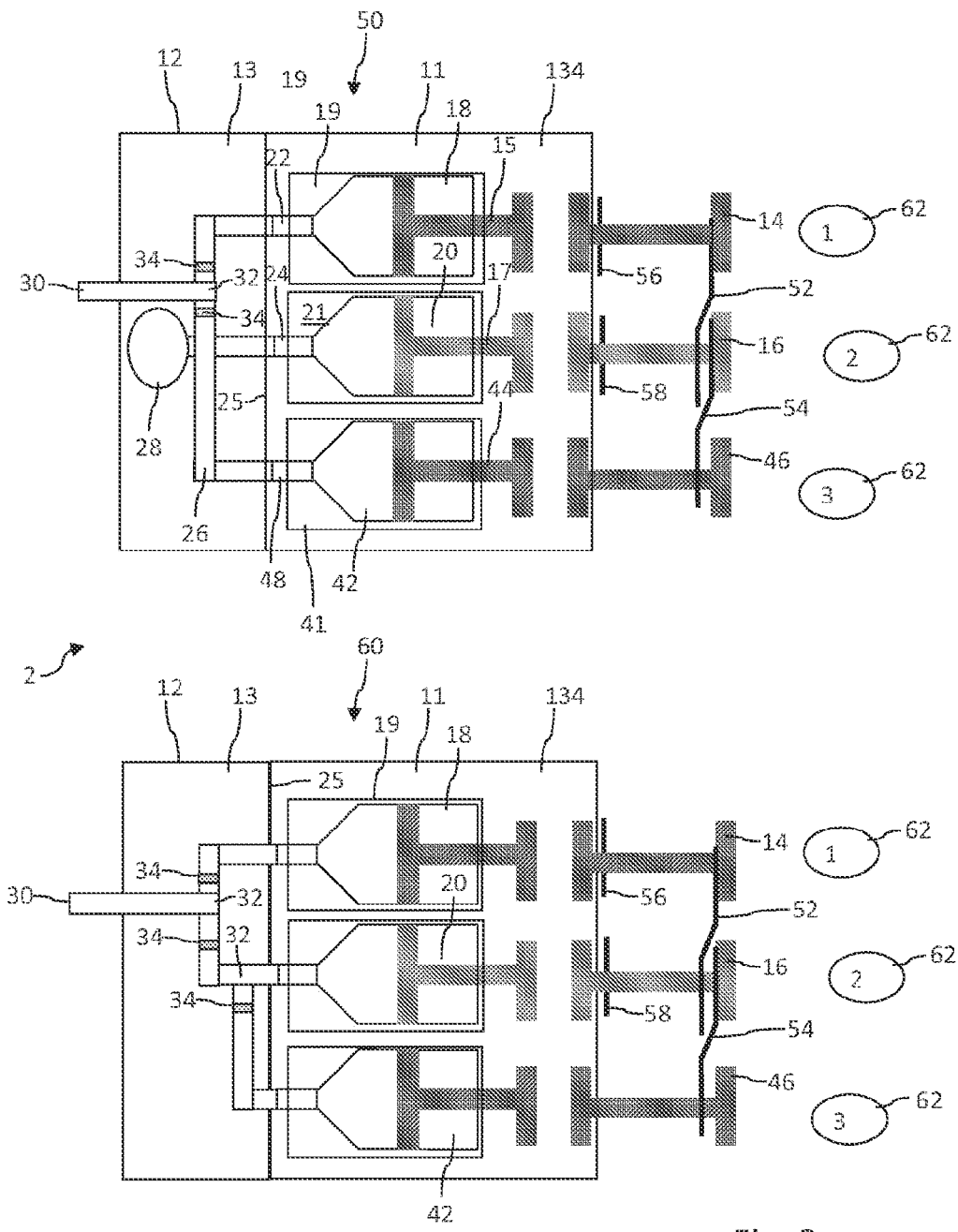
FIG. 2 shows another embodiment similar to the one of FIG. 1, wherein the blinding devices comprise three delivery devices.

The blinding kit 2 as shown in FIG. 2 features a structure substantially resembling the one of the blinding kit 1 according to FIG. 1. Therefore, identical reference numbers used throughout the set of Figures are universally used for identical or like components.

In contrast to the blinding kit 1 according to FIG. 1, the blinding kit 2 as shown in FIG. 2 features two blinding devices 50, 60, each of which having three delivery devices 18, 20, 42. The supplemental delivery device 42 is in permanent fluid communication with the delivery device 18. It is particularly intended to flush the tubing 26 downstream of the outlet ports 22, 24, 48 of the delivery devices 18, 20, 42. Also here, delivery device 42 is to be disposed and inserted into a receptacle 41 provided in the first compartment 11. Additionally, the delivery device 42 comprises a piston 44 mechanically engageable with a supplemental actuating member 46 extending through a side wall of the housing 12.

When appropriately inserted and disposed in the first compartment 11, the delivery devices 18, 20, 42 are in fluid communication with respective ports of the tubing 26 extending through the dividing wall 25. As illustrated in FIG. 2, the tubing 26 downstream of the outlet ports 22, 48 merge by means of a y-connector 32 being in direct fluid communication with the outlet 30. The outlet 24 of the medicament-containing delivery device 20 is in fluid communication with a collecting reservoir 28 disposed in the second compartment 13. The verum-type blinding device 60 differs from the above described placebo-type blinding device 50 in that all outlet ports 22, 24, 48 of the delivery devices 18, 20, 42 mutually merge, by way of two y-connectors 32.

Also here, upstream of the y-connectors 32, at least one check- or back-flow valve 34 is disposed on order to prevent back-flow into any of the delivery devices 18, 20, 42. Usage of the blinding devices 50, 60 is as follows.

After having established fluid interconnection of all three delivery devices 18, 20, 42 with the tubing 26 downstream thereof, in an initial step, the actuating member 14 is depressed in order to flush the tubing section 26. Thereafter, actuating member 16 operably engaged with the piston 17 of the delivery device 20 is depressed in order to dispense the medicament via the outlet 30 to the patient or in order to dispense the medicament into the collecting reservoir 28. Thereafter, the third actuating member 46 is depressed in order to repeatedly flush the downstream located tubing 26 and to entirely administer a residual portion of the medicament previously contained therein.

In order to enhance patient safety and to enforce accurate usage of the device, the actuating members 14, 16, 46 are interengaged by way of protecting elements 52, 54. This way, actuating member 46 cannot be depressed as long as actuating member 16 remains in its initial configuration. Similarly, protecting element 52 impedes actuation of the actuating member 16 as long as the actuating member 14 remains in its initial configuration as illustrated in FIG. 2. Moreover, actuating members 14, 16 are additionally equipped with securing pins 56, 58 in order to prevent that actuating member 14 is slaved by a depression of actuating member 16. Also, the various actuating members 14, 16, 46 may be colour encoded and may also be provided with a label 62 indicating the correct sequence and order the actuating members 14, 16, 46 should be depressed.

Figure 3:
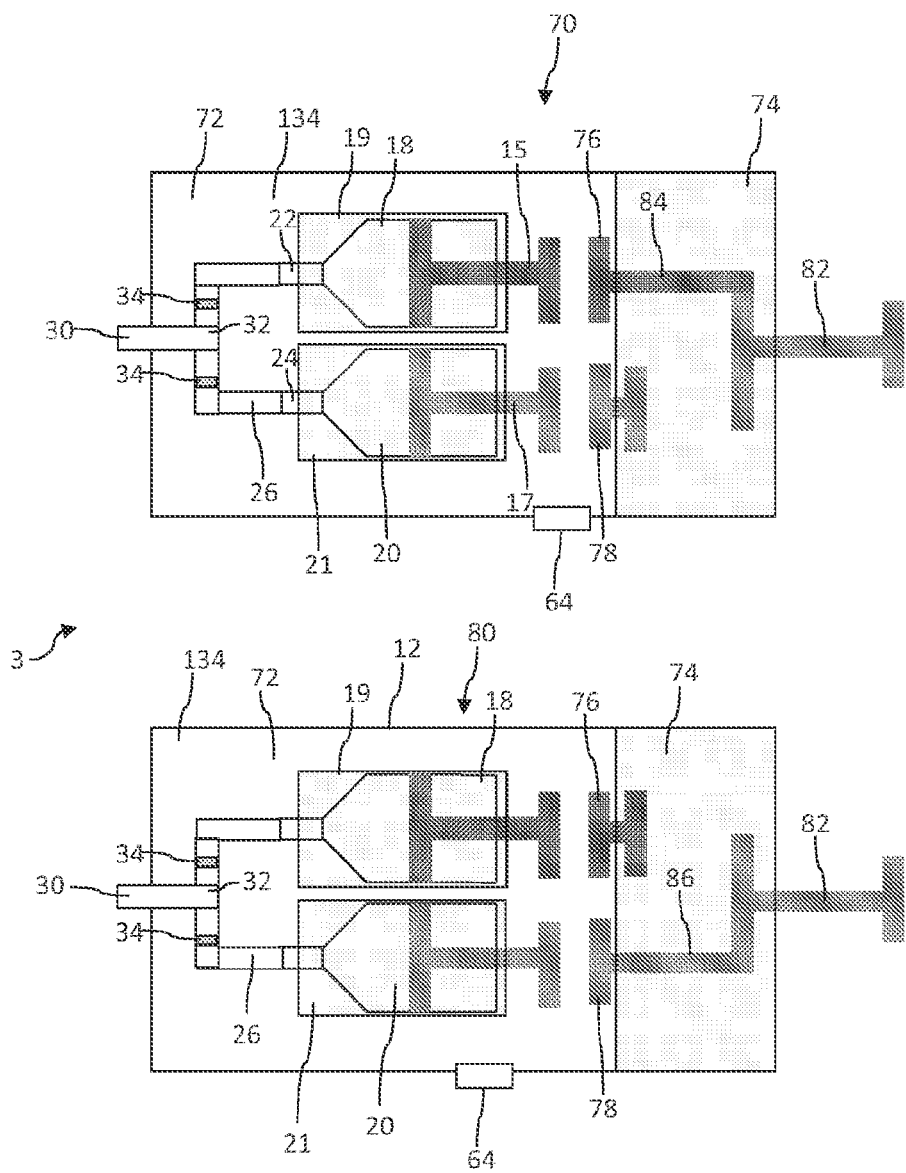
FIG. 3 is indicative of a further embodiment of a blinding kit, wherein a second compartment is adapted to conceal mechanical correlation between an actuating member and the two delivery devices of each blinding device.

FIG. 3 shows another embodiment of a blinding kit 3, wherein the housing 12 of a placebo-type blinding device 70 is divided in two compartments 72, 74, and wherein a second compartment 74 is adapted to conceal mechanical engagement and interaction between the actuating member 82 and the pistons 15, 17 of the delivery devices 18, 20. However, the tubing 26 downstream of the delivery devices 18, 20 can be designed identical for both, the placebo-type blinding device 70 as well as for the verum-type delivery device 80. Also here, the second compartment 74 is inaccessible and its interior is non-visible to a user or to medical staff.

The blinding devices 70, 80 each comprise two pressure pieces 76, 78 extending from the second compartment 74 into the first compartment 72. The pressure pieces 76, 78 are arranged in such a way, that a sliding motion thereof in distal direction, i.e. toward the outlet 22, 24 of the delivery devices 18, 20, leads to a respective distally directed displacement of pistons 15, 17 of the delivery devices 18, 20.

However and as illustrated with the blinding device 70, the actuating member 82 is only mechanically engaged and coupled with the pressure piece 76 via a transfer element 84. Consequently, distally directed depression of the actuating member 82 only induces dispensing of the content of the delivery device 18 typically filled with a physiologically inert solution. With the placebo-type blinding device 70, the pressure piece 78 is substantially effectless.

With the verum-type blinding device 72 in contrast, mechanical engagement between pressure pieces 76, 78 and the actuating member 82 is swapped. Here, the actuating member 82 is exclusively engaged or connected with the pressure piece 78 by way of the transfer element 86. This way, the verum-type blinding device is exclusively adapted to only dispense the substance contained in the delivery device 20.

Figure 6:
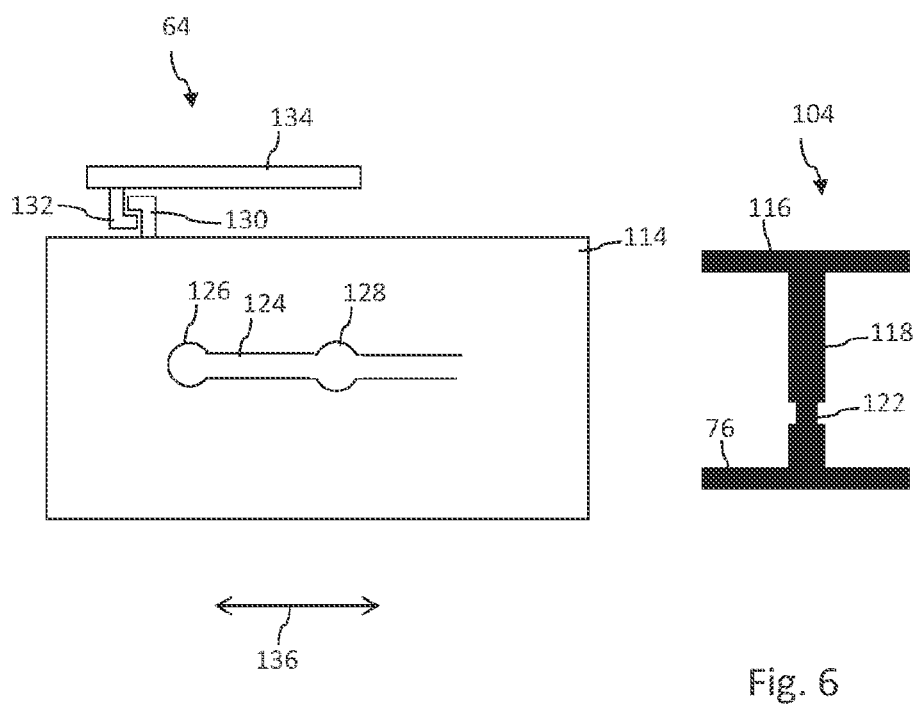
FIG. 6 is illustrative of a locking mechanism for a lid of a first compartment of the blinding devices.

The housing 12 in particular, the first compartment 11 adapted to receive the delivery devices 18, 20 is further equipped with an interlock 64 by way of which a lid 134 of the first compartment can be kept in a locked configuration as for instance shown in FIG. 6. Release of the interlock 64 is preferably coupled with the configuration and position of the actuating member 82. It is of particular benefit, when the actuating member 82 can be moved only when the lid 134 is closed. Otherwise, the pressure piece 76, 78 operably engaged with the actuating member 82 could be identified upon opening of the lid 134. In addition and in order to avoid the possibility to identify the type of device, once the lid is initially closed it should not be possible to re open the lid again. Hence the lid 134 is non-releasably attachable to the housing 12.

In order to entirely administer a predefined amount of a medicament contained in the delivery device 20, it is intended, that the delivery device 20 is slightly over-dosed in order to compensate the dead volume of the tubing 26 downstream the delivery device 20. Moreover, it is beneficial, when the blinding devices 70, 80 of the blinding kit 3 and in particular its downstream located tubing 26 is already flushed with e.g. an inert substance prior to its application in order to minimize a risk of injecting air or other substances located in the tubing 26. Therefore, the blinding devices 70, 80 and the blinding kit 3 is particularly adapted for use as a disposable blinding device readily equipped with pre-filled and/or with pre-assembled delivery devices 18, 20.

Figure 4:
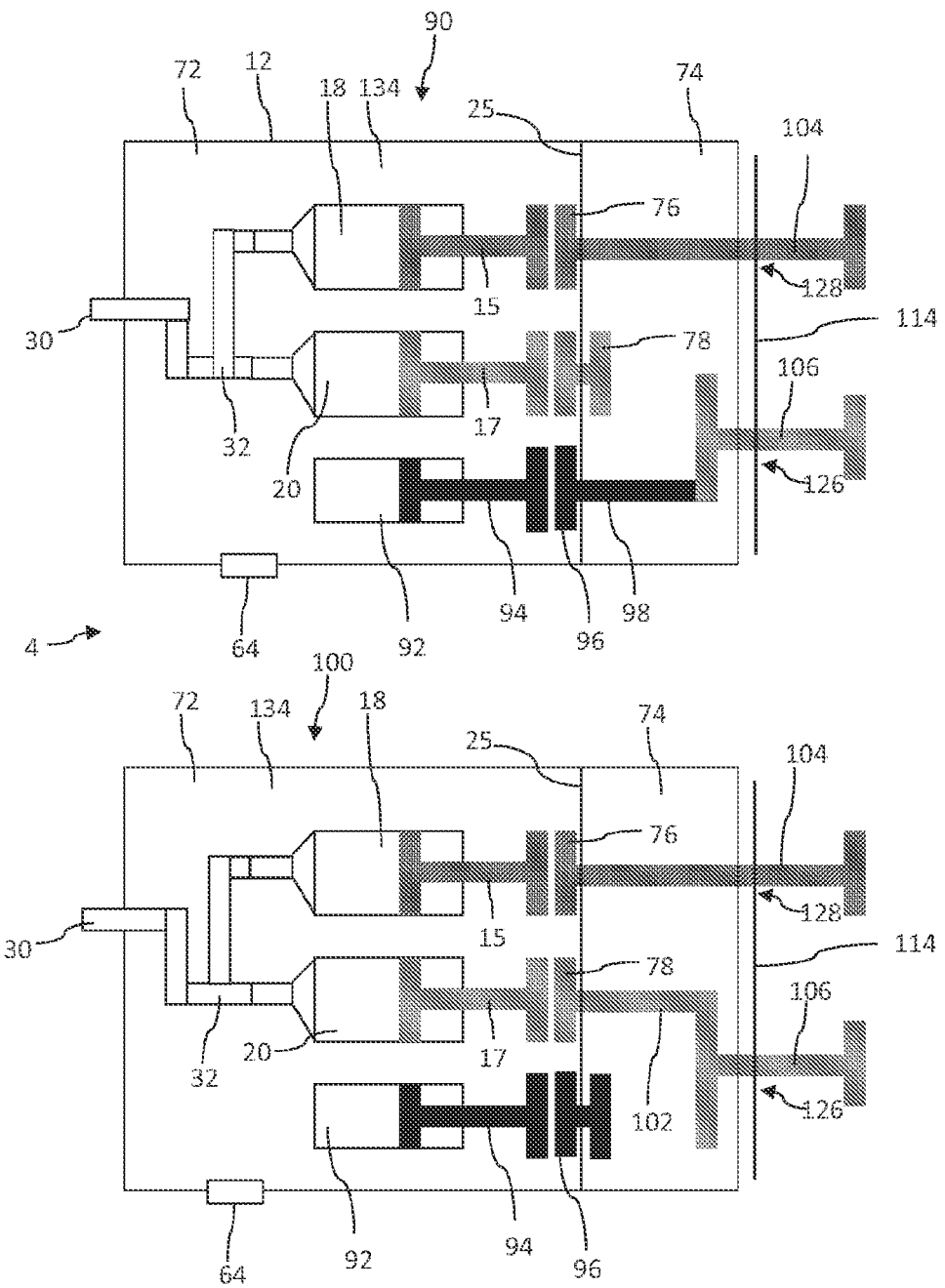
FIG. 4 shows another embodiment with a supplemental mock delivery device.

The blinding kit 4 as shown in FIG. 4 comprises a placebo-type blinding device 90 and a verum-type blinding device 100, each of which having a housing divided into a first compartment 72 and a second compartment 74. Similarly as already described with the blinding kit 3, the second compartment 74 is adapted to conceal mechanical interaction between actuating members 104, 106 and pistons 15, 17, 94 of delivery devices 18, 20, 92. In contrast to the blinding kit 3 as shown in FIG. 3, the blinding devices 90, 100 of the blinding kit 4 comprise a supplemental mock delivery device 92 which is not necessarily filled with a substance and which is not connected with the tubing 26 upstream of the outlet 30. However, the mock or dummy delivery device 92 comprises a piston 94 to cooperate with a correspondingly arranged pressure piece 96 extending through the dividing wall 25 which separates first and second compartments 72, 74.

Moreover, the blinding devices 90, 100 comprise two actuating members 104, 106, both extending outward from the housing 12. With both blinding devices 90, 100, the actuating member 104 is operably connected or operably engaged with the piston 15 of the delivery device 18, e.g. in order to flush the tubing 26 downstream thereof in an initial step. Thereafter, the actuating member 106 is to be depressed in order to expel and/or to dispense the medicament from the delivery device 20.

With the placebo-type blinding device 90, the dispensing device 20 is effectively disconnected and disengaged from the actuating member 106. Instead, the actuating member 106 is operably engaged with the piston 94 of the mock delivery device 92 via the transfer element 98. This way, a mechanical feedback and mechanical resistance can be provided to the actuating member 106 during its depression without dispensing any liquid substance. Hence, the pressure piece 78 of the placebo-type blinding device 90 is substantially ineffective.

In contrast to that, the verum-type blinding device 100 provides mechanical engagement between the actuating member 106 and the piston 17 of the delivery device 20 via the transfer element 102 and pressure piece 78. With this blinding device 100, dispensing of the medicament contained in and provided by the delivery device 20 is possible. Here, the mock delivery device 92 is substantially superfluous. However, since the compartment 72 may be accessible by opening of a lid 134, the internal structure of first compartments 72 of the two blinding devices 90, 100 should be substantially identical in order to prevent identification and unblinding of the particular devices. Alternatively, the mock devices 94 can be arranged in non-opening section of the device. It may further be sufficient when only the placebo-type blinding device 90 is equipped with the mock device 94.

Figure 5:
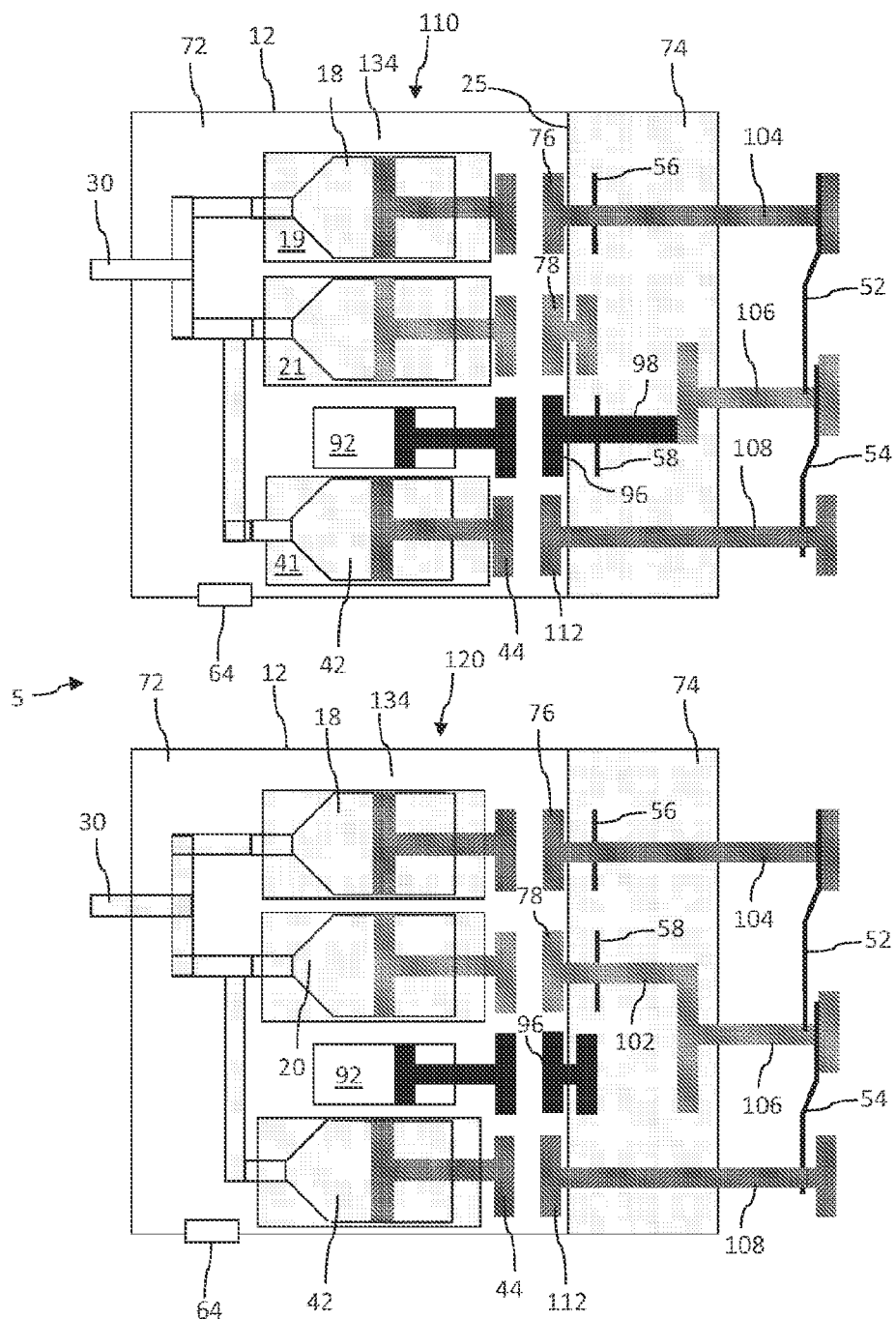
FIG. 5 shows a further embodiment, wherein each of the blinding devices comprises three delivery devices and a mock device.

FIG. 5 further illustrates another embodiment of a blinding kit, wherein the principle of use of a mock delivery device 92 as described for instance with respect to the blinding kit 4 is transferred to an embodiment, wherein the two blinding devices 110, 120 comprise three delivery devices 18, 20, 42, each of which being filled with a dispensable substance and wherein the blinding devices 110, 120 comprise a supplemental but mock delivery device 92 in order to imitate mechanical feedback and/or mechanical resistance of displacement of a piston 15, 17 inside a barrel of the delivery device 18, 20, respectively.

Similar, as already explained in view of the blinding kit 4 as shown in FIG. 4, the placebo-type blinding device 110 and the verum-type blinding device 120 only differ by their actuating member 106 and its mechanical engagement with either a mock delivery device 92 or with a real or genuine dispensing device 20. Supplemental to the embodiment according to FIG. 4, the blinding kit further comprises a third delivery device 42 operably engageable with an additional actuating member 108 which extends through the second compartment 74 with a pressure piece 112 to cooperate with a piston 44 of the delivery device 42.

In the same way as already described with respect to the embodiment shown in FIG. 2, the various delivery devices 18, 20, 42 are in fluid communication downstream of their outlet ports 22, 24, 48 by way of a tubing system 26 and by way of two y-connectors 32 associated with back-flow or check-valves 34. Additionally and as already described in connection with the blinding kit 2 as shown in FIG. 2, the actuating members 104, 106, 108 may also be mechanically engaged by means of protecting elements 52, 54 as well as by way of securing pins 56, 58.

Additionally, and universally applicable to any embodiment, wherein the second compartment 74 serves to accommodate and to conceal mechanical interaction between actuating members 104, 106, 108 and respective delivery devices 18, 20, 92, 42, FIG. 4 schematically illustrates a slide member 114 slideably disposed at the outside facing side wall of the housing 12. The slide member 114 as illustrated in FIG. 6 from a side view comprises a longitudinal slit 124 extending along a sliding direction 136. The slit 124 comprises two recesses or widened portions 126, 128 that match with the diameter of a shaft 118 of the pressure piece 104 as it extends through the side wall of the housing 12.

The shaft 118 further comprises a groove 122 which matches with the size of the slit 124. This way at the opened position of the lid 134 the actuating member 104, 106, 108 cannot be moved as the grooves are positioned in the slit at position 124. Only at the closed position of the lid 134, the shaft 118 matches with the widened positions 126, 128. Therefore, only in this position the actuating member 104, 106, 108 can be moved.

However, when the lid is not in its closed position or configuration, a motion of the actuating member 104, 106, 108 relative o the housing 12 is substantially impeded because the diameter of the shaft 118 is larger than the width of the slit 124. Furthermore, the slide 114 comprises a latch element 130 adapted to engage with a corresponding counter-latch element 132 being operably connected to or with the lid 134. This way, a mechanical coupling between an interlock mechanism of the lid 134 and a position of the actuating member 104 can be provided. In addition, this system of 130 and 132 can be designed in that way that the device cannot be opened again in order to avoid unblinding. The type of device could be identified after a final use by opening the respective device. With the placebo-type blinding device the medicament, if initially present, is still available whereas the medicament has been used or consumed with the verum-type blinding device.

In FIGS. 7a and 7b another embodiment of a blinding kit 6 featuring a single type of blinding device 200 is shown. The blinding device 200 comprises a first compartment 201 and a second compartment 203. The first compartment 201 is adapted to receive at least two delivery devices 18, 20 while the second compartment 203 is equipped with two actuating members 14, 16 extending into the first compartment 201. Additionally, there are provided two electrical drives 212, 214 operably engaged with the actuating members 14, 16 in order to apply thrust to the delivery devices 18, 20.

The delivery devices 18, 20 are provided as integral parts of a tube system 202 further featuring a four-way valve 216. As illustrated in FIG. 7b the valve 216 is operable to interconnect the delivery device 18 with the outlet 30 via a tube 206. In another configuration but not illustrated, the valve 216 may be equally adapted to separately connect the delivery device 20 with the outlet 30. From the configuration according to FIG. 7b this could be achieved by a counter clockwise rotation by 90°.

In the configuration according to 7a the valve is in neutral position wherein both fluid transferring ports of the valve 216 are disconnected from any of the tubes 204, 206, 208, 30 interconnected to a valve housing.

As further illustrated in FIGS. 7a and 7b the valve 216, currently implemented as a four-way valve, may also be connected and coupled with a collecting reservoir 28 via a tube 208.

Preferably, the valve 216 is remotely actuatable by means of the control unit 210, which may also control and selectively actuate the electrical drives 212, 214.

In this way, various dispensing or administration schemes may be implemented. For instance, at the beginning of a treatment procedure the valve 216 may be configured to interconnect the delivery device 18 with the outlet 30 in a fluid transferring way. Then, the respective electrical drive 212 can be activated in order to dispense a predefined amount of the product of the delivery device 18 through the outlet 30.

Thereafter, and depending on whether the respective patient should receive a pharmaceutically active or pharmaceutically inactive substance, the valve 216 may be switched in order to disconnect the delivery device 18 from the outlet 30 and to connect the delivery device 20 with the outlet 30. If for instance the delivery device 20 is provided with the pharmaceutically active substance, said substance can be dispensed to the patient by activating the electrical drive 214.

After a respective dispensing procedure has terminated the valve 216 may return into the configuration according to FIG. 7b. Then, the injection port connected with the patient could for instance be flushed with a physiologically inert or pharmaceutically inert substance by repeatably activating the electrical drive 212.

Thereafter, and in order to completely empty also the delivery device 18 the valve could be switched into a configuration wherein the content of the delivery device 18 can be dispensed into the collecting reservoir 28. In a similar and corresponding way, the procedure may also be conducted when a placebo-type of blinding device should be implemented.

At the end of an administering procedure the electrical drives 212, 214 as well as the actuating members 14, 16 may return into an initial configuration leaving the two dispensed and emptied delivery devices 18, 20 in the compartment 201. Then, the entire tube system 202 comprising the delivery devices 18, 20, the collecting reservoir 28, the valve 216, as well as the outlet 30 and the various tubes 204, 206, 208 could be replaced by a new tube system 202.

Actuation of the valve 216 as well as actuation of the electrical drives 212, 214 can be controlled and governed by the control unit 210. Moreover, the control unit 210 may individually decide according to e.g. a patient identification number whether the blinding device 200 should be driven in placebo- or verum-mode. The control unit 210 may then be operable to conduct a respective dispensing procedure.

The invention claimed is:

1. A blinding kit for administering a substance to a patient in a clinical trial, the blinding kit comprising:
   a first blinding device and a second blinding device, wherein each of the first and second blinding devices comprises:
   an opaque housing to entirely enclose at least two delivery devices wherein an inert substance is provided in a first delivery device of the at least two delivery devices, and wherein a pharmaceutically active substance is provided in a second delivery device of the at least two delivery devices, an outlet being in fluid communication with at least one of the first and the second delivery devices for administering the substance to the patient, wherein the substance is either the inert substance or the pharmaceutically active substance, and at least one actuating member of piston type extending outside and through the housing, wherein the at least one actuating member is mechanically engageable with one of the at least two delivery devices such that the at least one actuating member is actuatable from outside the housing, wherein a) the first blinding device is adapted to impede dispensing of the pharmaceutically active substance from the second delivery device to the outlet in response to an actuation of the at least one actuating member of the first blinding device or b) wherein the at least one actuating member of the first blinding device is coupled to the first delivery device and is decoupled from the second delivery device of the first blinding device, and wherein the at least one actuating member of the second blinding device is decoupled from the first delivery device and is coupled to the second delivery device of the second blinding device.

2. The blinding kit according to claim 1, comprising at least two actuating members extending outside the housing, wherein each one of the actuating members is mechanically engageable with only one of the at least two delivery devices.

3. The blinding kit according to claim 1, wherein the housing comprises a first compartment and a second compartment separated from each other, wherein the first compartment is adapted to receive the at least two delivery devices.

4. The blinding kit according to claim 3, wherein the first compartment comprises at least two receptacles being mechanically encoded to exclusively receive a particular type of delivery device.

5. The blinding kit according claim 3, wherein the first compartment is accessible through a lockable lid for inserting or exchanging at least one delivery device.

6. The blinding kit according to claim 3, wherein the second compartment is inaccessible and is further adapted to conceal a correlation between the at least one actuating member and a flow path upstream of the outlet.

7. The blinding kit according to claim 6, wherein the second compartment is arranged downstream of the at least two delivery devices and provides a fluid communication between at least one of the delivery devices and the outlet.

8. The blinding kit according to claim 3, wherein the second compartment further comprises a collecting reservoir to be coupled with at least the second delivery device of the first blinding device in a fluid transferring way to receive or to collect the pharmaceutically active substance dispensable by the second delivery device.

9. The blinding kit according to claim 3, wherein the second compartment comprises at least one mechanical transfer element mechanically engaged with the at least one actuating member and being further mechanically engageable with at least one of the delivery devices.

10. The blinding kit according to claim 9, wherein the transfer element is slidably disposed in the second compartment and extends into the adjacently arranged first compartment with a pressure piece.

11. The blinding kit according to claim 1, wherein the first compartment comprises a mock delivery device operably engageable with at least one actuating member and being adapted to imitate a mechanical resistance of the first delivery device when operated.

12. The blinding kit according to claim 1, wherein the first blinding device comprises a collecting reservoir to receive or to collect the pharmaceutically active substance dispensable from the second delivery device coupled therewith, and wherein the second blinding device provides a fluid communication between the first delivery device and the outlet.

13. The blinding kit according to claim 1, wherein the at least one actuating member of the first and second blinding devices comprise actuating members of substantially identical appearance outside the housing, wherein the the second delivery device of the first blinding device is operably disengaged from a first actuating member of the first blinding device while the first delivery device of the second blinding device is operably engaged with a first actuating member of the second blinding.

* * * * *